(12) United States Patent
Watanabe

(10) Patent No.: US 11,010,891 B2
(45) Date of Patent: May 18, 2021

(54) MEDICAL IMAGE PROCESSING APPARATUS, ENDOSCOPE APPARATUS, DIAGNOSTIC SUPPORT APPARATUS, AND MEDICAL SERVICE SUPPORT APPARATUS

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 385 days.

(21) Appl. No.: 16/109,677

(22) Filed: Aug. 22, 2018

(65) Prior Publication Data

US 2019/0073769 A1   Mar. 7, 2019

(30) Foreign Application Priority Data

Sep. 1, 2017   (JP) .............................. JP2017-168754

(51) Int. Cl.
*G06T 7/00* (2017.01)
*A61B 5/00* (2006.01)
(Continued)

(52) U.S. Cl.
CPC ........ *G06T 7/0012* (2013.01); *A61B 1/00009* (2013.01); *A61B 1/00045* (2013.01);
(Continued)

(58) Field of Classification Search
CPC ................. G06T 7/0012; G06T 7/246; G06T 2207/30096; G06T 7/0016;
(Continued)

(56) References Cited

U.S. PATENT DOCUMENTS 6,588,901 B1   7/2003   Grinvald et al.
7,670,286 B2   3/2010   Imaizumi et al.
(Continued)

FOREIGN PATENT DOCUMENTS

AU         738223     9/2001
EP        1494579     1/2005
(Continued)

OTHER PUBLICATIONS

"Office Action of Japan Counterpart Application", dated Aug. 25, 2020, with English translation thereof, p. 1-p. 6.
(Continued)

*Primary Examiner* — Pascal M Bui Pho
*Assistant Examiner* — Bele Alex
(74) *Attorney, Agent, or Firm* — JCIPRNET

(57) ABSTRACT

There are provided a medical image processing apparatus, an endoscope apparatus, a diagnostic support apparatus, and a medical service support apparatus capable of detecting red blood cells using an endoscope image. A medical image processing apparatus includes: a medical image acquisition unit that acquires short wavelength medical images, which are medical images including a subject image and which are obtained by imaging a subject with light in a shorter wavelength band than a green wavelength band; and a red blood cell detection unit that detects red blood cells using the short wavelength medical images. The light in the short wavelength band is, for example, light in a blue band or a violet band of a visible range. The red blood cell detection unit detects, for example, a high-frequency, granular, and high-density region as red blood cells.

15 Claims, 10 Drawing Sheets

(51) Int. Cl.
*A61B 1/00* (2006.01)
*A61B 5/145* (2006.01)
*A61B 5/1459* (2006.01)
*G06T 7/246* (2017.01)
*A61B 1/06* (2006.01)
*A61B 1/31* (2006.01)
*A61B 5/026* (2006.01)
*G06K 9/00* (2006.01)
*G16H 30/20* (2018.01)
*G16H 40/63* (2018.01)
*G16H 30/40* (2018.01)

(52) U.S. Cl.
CPC .............. *A61B 1/0638* (2013.01); *A61B 1/31* (2013.01); *A61B 5/0084* (2013.01); *A61B 5/0261* (2013.01); *A61B 5/1459* (2013.01); *A61B 5/14503* (2013.01); *A61B 5/14535* (2013.01); *A61B 5/4842* (2013.01); *A61B 5/743* (2013.01); *G06K 9/00134* (2013.01); *G06T 7/0016* (2013.01); *G06T 7/246* (2017.01); *G06T 2207/10016* (2013.01); *G06T 2207/10024* (2013.01); *G06T 2207/10068* (2013.01); *G06T 2207/30028* (2013.01); *G06T 2207/30096* (2013.01); *G06T 2207/30104* (2013.01); *G06T 2207/30242* (2013.01); *G16H 30/20* (2018.01); *G16H 30/40* (2018.01); *G16H 40/63* (2018.01)

(58) Field of Classification Search
CPC . G06T 2207/10016; G06T 2207/10024; G06T 2207/10068; G06T 2207/30028; G06T 2207/30104; G06T 2207/30242; G06T 2207/10004; G06K 9/00134; G16H 30/20; G16H 30/40; G16H 40/63; A61B 1/00045; A61B 1/0638; A61B 1/31; A61B 5/0084; A61B 5/0261; A61B 5/14503; A61B 5/14535; A61B 5/1459; A61B 5/4842; A61B 5/743; A61B 1/04; A61B 1/00009; A61B 1/07; A61B 1/05; A61B 1/0669

See application file for complete search history.

(56) References Cited

U.S. PATENT DOCUMENTS

| | | | |
|---|---|---|---|
| 7,912,534 | B2 | 3/2011 | Grinvald et al. |
| 8,323,197 | B2 | 12/2012 | Kono et al. |
| 8,521,260 | B2 | 8/2013 | Grinvald et al. |
| 9,820,650 | B2 | 11/2017 | Uji et al. |
| 9,959,618 | B2* | 5/2018 | Kitamura .............. A61B 5/4255 |
| 10,231,600 | B2 | 3/2019 | Ikemoto et al. |
| 10,231,658 | B2 | 3/2019 | Shiraishi |
| 10,736,499 | B2 | 8/2020 | Yamanashi et al. |
| 2005/0131284 | A1 | 6/2005 | Grinvald et al. |
| 2008/0021331 | A1* | 1/2008 | Grinvald .............. A61B 5/1459 600/476 |
| 2013/0070077 | A1 | 3/2013 | Winkelman et al. |
| 2014/0320620 | A1* | 10/2014 | Ikemoto ............... A61B 1/0005 348/71 |
| 2015/0181185 | A1* | 6/2015 | Ikemoto ............... A61B 1/0684 348/71 |

FOREIGN PATENT DOCUMENTS

| | | | |
|---|---|---|---|
| EP | 2772184 A1 * | 9/2014 | .......... A61B 3/1241 |
| JP | S5230493 | 3/1977 | |
| JP | 2002517269 | 6/2002 | |
| JP | 2005006768 | 1/2005 | |
| JP | 2005521499 | 7/2005 | |
| JP | 2006519032 | 8/2006 | |
| JP | 2008104628 | 5/2008 | |
| JP | 2008302095 | 12/2008 | |
| JP | 2010187925 | 9/2010 | |
| JP | 2014166270 | 9/2014 | |
| JP | 2016154588 | 9/2016 | |
| JP | 2017067524 | 4/2017 | |
| JP | 2017122431 | 7/2017 | |
| WO | WO-9963882 A1 * | 12/1999 | ............. G01P 5/001 |
| WO | 2015045576 | 4/2015 | |

OTHER PUBLICATIONS

"Search Report of Europe Counterpart Application", dated Jan. 11, 2019, p. 1-p. 7.

* cited by examiner

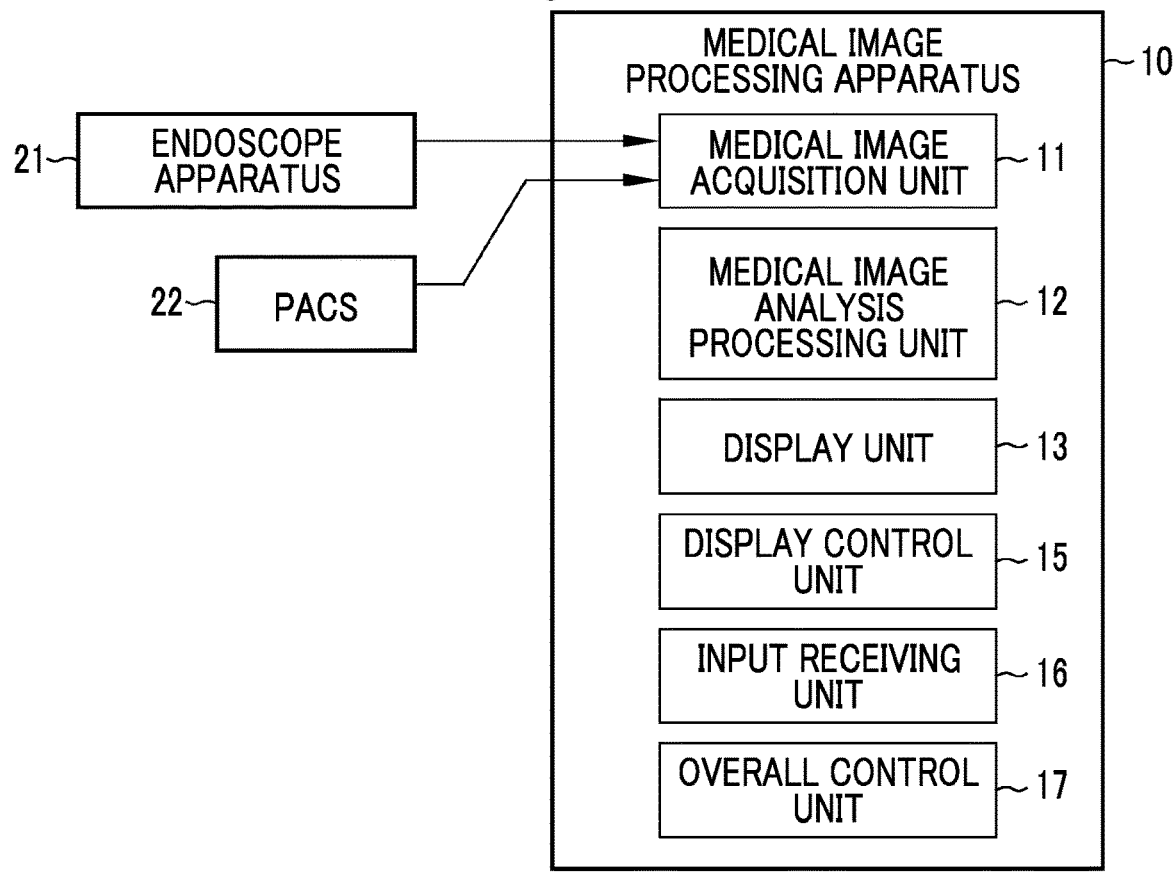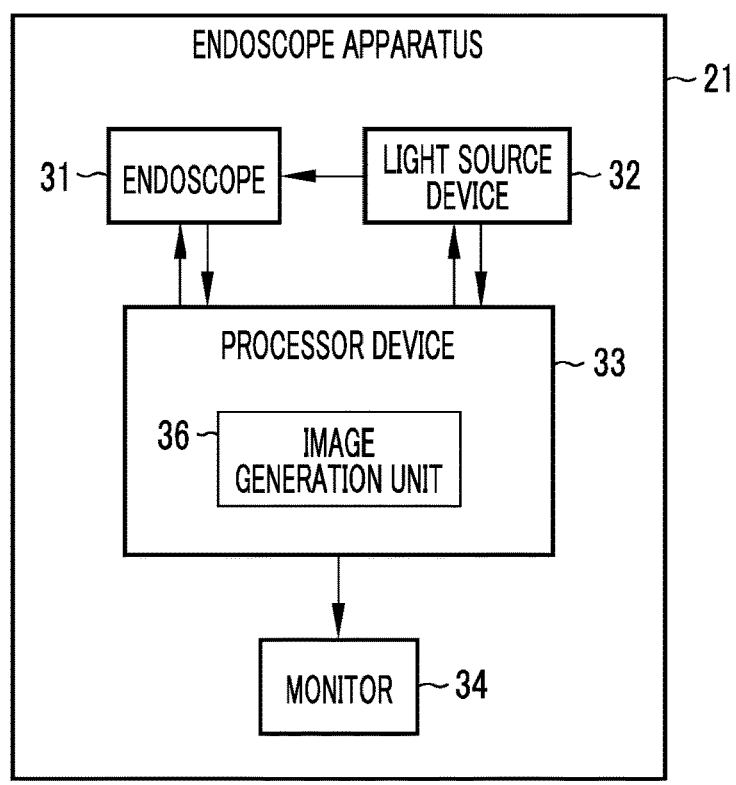

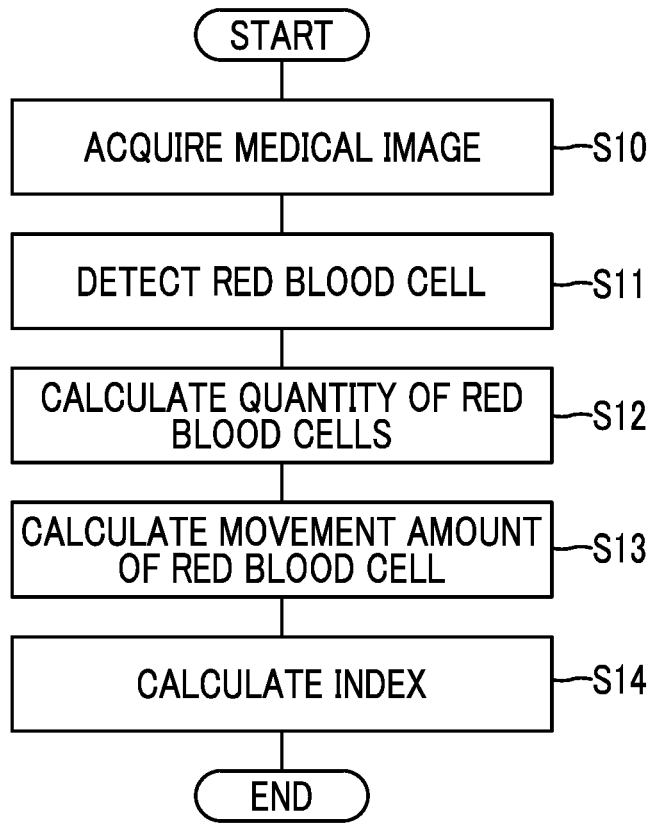
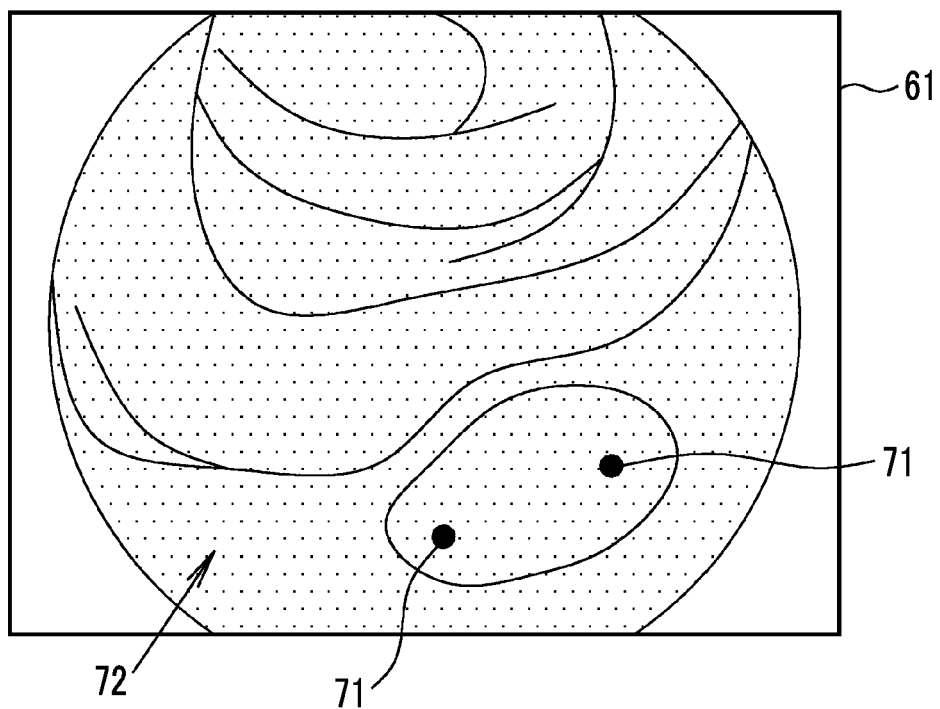

MEDICAL IMAGE PROCESSING APPARATUS, ENDOSCOPE APPARATUS, DIAGNOSTIC SUPPORT APPARATUS, AND MEDICAL SERVICE SUPPORT APPARATUS

CROSS-REFERENCE TO RELATED APPLICATIONS

The present application claims priority under 35 U.S.C. § 119 to Japanese Patent Application No. 2017-168754, filed on Sep. 1, 2017. Each of the above application(s) is hereby expressly incorporated by reference, in its entirety, into the present application.

BACKGROUND OF THE INVENTION

1. Field of the Invention

The present invention relates to a medical image processing apparatus, an endoscope apparatus, a diagnostic support apparatus, and a medical service support apparatus that use analysis results of medical images.

2. Description of the Related Art

In the related art, an apparatus relevant to medical care (hereinafter, referred to as a medical apparatus) that acquires an image (hereinafter, referred to as a medical image) of a subject presents the acquired medical image to a doctor. Then, the doctor performs diagnosis or the like using the medical image obtained from the medical apparatus as one of the determination materials. Needless to say, the determination of the state of the subject or the like that is performed by using the medical image at the time of diagnosis is based on the skill, experience, and the like of the doctor.

In recent years, since image analysis technology has advanced, various types of objective information can be acquired from medical images by analyzing the medical images. For this reason, the number of medical apparatuses that support determination, diagnosis, and the like by presenting the analysis results of medical images to a doctor or the like has been increasing. In addition, an endoscope apparatus that specifies the movement speed of blood or the movement direction of blood and outputs data indicating the distribution of the movement speed of blood or the movement direction of blood is known (JP2010-187925A).

SUMMARY OF THE INVENTION

Recent medical apparatuses are required to present the analysis results of medical images. However, depending on the type of lesion, the degree of progress, or the like, analysis results relevant to the presence or absence of a lesion or the degree of progress (so-called stage) may not be able to be easily obtained. Specifically, in diagnosis using an endoscope image, it may be difficult to obtain an accurate analysis result from which the degree of progress of an inflammatory disease can be determined.

Incidentally, there are cases where the flow of blood is useful for determining the presence or absence of a lesion, the degree of progress, or the like. Therefore, as long as blood, in particular, red blood cells containing blood can be detected in an endoscope image, an analysis result from which the degree of progress of an inflammatory disease can be determined more accurately than in the related art may be obtained.

Although the invention according to JP2010-187925A detects the movement speed or the movement direction of red blood cells, a very limited subject is reflected on the used endoscope image. For this reason, it is difficult to detect red blood cells from endoscope images, which are captured by other endoscopes for imaging the digestive tract and the like, using the method used in the invention according to JP2010-187925A.

Specifically, the red blood cell detected by the invention according to JP2010-187925A is a red blood cell flowing through a capillary vessel having a thickness of almost one red blood cell called a glomerulus. In addition, in the invention according to JP2010-187925A, a filamentous body is irradiated with broadband light including at least a green wavelength band, and is imaged through a green color filter. However, in the endoscope image obtained by imaging the digestive tract and the like, in the case of emitting broadband light including the green wavelength band, it is difficult to detect red blood cells even in a case where the subject is imaged through the green color filter.

It is an object of the invention to provide a medical image processing apparatus, an endoscope apparatus, a diagnostic support apparatus, and a medical service support apparatus capable of detecting red blood cells using an endoscope image obtained by imaging the large intestine or the like.

A medical image processing apparatus of the invention comprises: a medical image acquisition unit that acquires a short wavelength medical image, which is a medical image including a subject image and which is obtained by imaging a subject with light in a shorter wavelength band than a green wavelength band; and a red blood cell detection unit that detects a red blood cell using the short wavelength medical image.

It is preferable that the red blood cell detection unit detects a high-frequency, granular, and high-density region as a red blood cell using the short wavelength medical image.

It is preferable to further comprise: a red blood cell quantity calculation unit that calculates a quantity of red blood cells detected in the short wavelength medical image; a red blood cell movement amount calculation unit that calculates a movement amount of red blood cells detected in the short wavelength medical image; and an index calculation unit that calculates an index indicating a degree of progress of a lesion using the quantity and the movement amount of red blood cells.

It is preferable that the red blood cell movement amount calculation unit calculates the movement amount of red blood cells using a series of the short wavelength medical images in which red blood cells are detected by the red blood cell detection unit.

It is preferable that the red blood cell movement amount calculation unit calculates the movement amount of red blood cells using two of the short wavelength medical images captured consecutively or two of the short wavelength medical images captured at specific intervals.

It is preferable that the index calculation unit calculates the index correlated with a degree of progress of an inflammatory bowel disease.

It is preferable that the index calculation unit calculates the index by weighting addition of the quantity and the movement amount.

It is preferable to further comprise: a display unit that displays the short wavelength medical image; and a display control unit that adjusts a display color of the short wavelength medical image displayed on the display unit.

It is preferable that the display control unit sets a color of a mucous membrane as a green color.

It is preferable to further comprise a display unit that displays the degree of progress of the lesion and the index so as to be associated with each other.

It is preferable to further comprise a region of interest detection unit that detects a region of interest, which is a region to be observed, based on a feature amount of pixels of the short wavelength medical image. It is preferable that the red blood cell detection unit detects a red blood cell in the region of interest.

It is preferable that the short wavelength medical image is an image obtained by emitting light in a specific wavelength band.

It is preferable that the specific wavelength band is a blue band or a violet band of a visible range.

It is preferable that the light in the specific wavelength band has a peak at 390 nm or more and 450 nm or less.

An endoscope apparatus of the invention comprises: the medical image processing apparatus described above; and an endoscope that acquires an image by emitting light in the short wavelength band.

A diagnostic support apparatus of the invention comprises the medical image processing apparatus described above.

A medical service support apparatus of the invention comprises the medical image processing apparatus described above.

The medical image processing apparatus, the endoscope apparatus, the diagnostic support apparatus, and the medical service support apparatus of the invention can detect red blood cells using an endoscope image obtained by imaging the large intestine or the like.

BRIEF DESCRIPTION OF THE DRAWINGS

FIG. 1 is a block diagram of a medical image processing apparatus.

FIG. 2 is a block diagram of an endoscope apparatus.

FIG. 5 is a flowchart showing the operation of the medical image processing apparatus.

FIG. 6 is a short wavelength medical image captured first between a series of short wavelength medical images.

DESCRIPTION OF THE PREFERRED EMBODIMENTS

Figure 3:
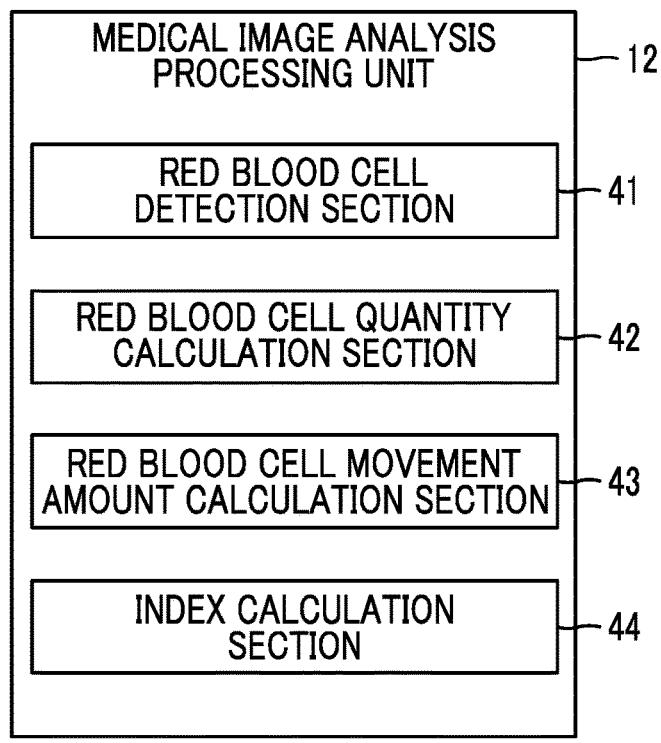
FIG. 3 is a block diagram of a medical image analysis processing unit.

As shown in FIG. 1, a medical image processing apparatus 10 includes a medical image acquisition unit 11, a medical image analysis processing unit 12, a display unit 13, a display control unit 15, an input receiving unit 16, and an overall control unit 17.

The medical image acquisition unit 11 acquires an endoscope image (hereinafter, referred to as a medical image), which is a medical image including a subject image, directly from an endoscope apparatus 21 that is a medical apparatus or through a management system, such as a picture archiving and communication system (PACS) 22, or other information systems. The medical image is a still image or a motion picture. In a case where the medical image is a motion picture, the display of the medical image includes not only displaying a still image of one representative frame forming the motion picture but also reproducing the motion picture once or multiple times.

In the case of acquiring a plurality of types of medical images, the medical image acquisition unit 11 acquires at least short wavelength medical images 61 and 62 (refer to FIGS. 6 and 7) among these medical images. The short wavelength medical images 61 and 62 are medical images obtained by imaging the subject with light in a shorter wavelength band than the green wavelength band. The "green wavelength band" refers to a wavelength band of about 500 nm or more and 570 nm or less. The "wavelength band shorter than the green wavelength band" refers to a wavelength less than about 500 nm. Accordingly, the short wavelength medical images 61 and 62 acquired by the medical image acquisition unit 11 are medical images obtained by imaging the subject using light containing components in a wavelength band substantially less than about 500 nm as illumination light. However, the illumination light used for imaging the short wavelength medical images 61 and 62 can contain a component in a wavelength band of about 500 nm or more (green light) in addition to a component in a wavelength band less than about 500 nm to the extent that the characteristics of the subject image are not lost in the case of imaging the subject using light in a wavelength band less than about 500 nm. For example, the medical image acquisition unit 11 acquires a short wavelength medical image captured by using, as illumination light, narrow band light in a very narrow wavelength band (for example, about ±10 nm) in which the peak is in the range of 390 nm to 450 nm, the medical image analysis processing unit 12 uses the short wavelength medical images 61 and 62.

The medical image acquisition unit 11 acquires a series of short wavelength medical images 61 and 62. The series of short wavelength medical images 61 and 62 refer to the two short wavelength medical images 61 and 62 captured consecutively or the two short wavelength medical images 61 and 62 captured at specific intervals. More specifically, in the case of a still image, the series of short wavelength medical images 61 and 62 are two or more medical images obtained by sequentially imaging the same subject in one examination. In the case of a motion picture, the series of short wavelength medical images 61 and 62 are medical images of two or more frames contained in the motion picture or medical images of two or more frames that can be freely acquired from a plurality of motion pictures obtained by sequentially imaging the same subject in one examination. In a case where the short wavelength medical image of the still image and the short wavelength medical image of one or more frames included in the motion picture are obtained by sequentially imaging the same subject in one examination, the medical image acquisition unit 11 can acquire these as a series of short wavelength medical images. The imaging interval between individual short wavelength medical images included in a series of short wavelength medical images can be freely set or selected. In the present embodiment, the medical image acquisition unit 11 acquires the short wavelength medical image 61 (refer to FIG. 6), which is captured first, and the short wavelength medical image 62 (refer to FIG. 7), which is captured after the short wavelength medical image 61, along the time series of imaging.

In a case where there are a plurality of medical images in the endoscope apparatus 21, the PACS 22, or the like, the medical image acquisition unit 11 can select and acquire all or some (for example, only short wavelength medical images) of the plurality of medical images. In the case of selecting and acquiring some medical images from the plurality of medical images in the endoscope apparatus 21, the PACS 22, or the like, it is possible to manually select a medical image in accordance with a user operation of a doctor or the like. The medical image acquisition unit 11 can automatically select a medical image to be acquired according to the imaging date and time, an imaging part, or other conditions set in advance (for example, the type of illumination light used for imaging).

In the present embodiment, the medical image processing apparatus 10 is connected to the endoscope apparatus 21 to acquire a medical image from the endoscope apparatus 21. As shown in FIG. 2, in the present embodiment, the endoscope apparatus 21 to which the medical image processing apparatus 10 is connected has an endoscope 31 that acquires an image by emitting at least one of light in a white wavelength band or light in a specific wavelength band to image the subject, a light source device 32 that emits illumination light to the inside of the subject through the endoscope 31, a processor device 33, and a monitor 34 for displaying an endoscope image or the like captured by using the endoscope 31. The light in a specific wavelength band that is used as illumination light by the endoscope 31 is, for example, light in a shorter wavelength band than the green wavelength band. In particular, the light in a specific wavelength band is light in a blue band or a violet band of the visible range. The processor device 33 includes an image generation unit 36 that generates an endoscope image. The medical image processing apparatus 10 is connected to the processor device 33. The medical image acquisition unit 11 acquires the short wavelength medical images 61 and 62 directly from the image generation unit 36 of the endoscope apparatus 21.

The medical image analysis processing unit 12 performs analysis processing using the short wavelength medical images 61 and 62 acquired by the medical image acquisition unit 11. Specifically, as shown in FIG. 3, the medical image analysis processing unit 12 includes a red blood cell detection section 41, a red blood cell quantity calculation section 42, a red blood cell movement amount calculation section 43, and an index calculation section 44.

The red blood cell detection section 41 detects a red blood cell 71 (refer to FIG. 6 and the like) using the short wavelength medical images 61 and 62. The detection target of the red blood cell detection section 41 is a mass (collection) in which one red blood cell 71 or a plurality of red blood cell 71 gather. Specifically, the red blood cell detection section 41 detects a high-frequency, granular, and high-density region as the red blood cell 71 (or the mass of the red blood cells 71; the same hereinbelow) using the short wavelength medical images 61 and 62.

The term "high frequency" refers to a higher spatial frequency than the spatial frequency of a structure such as a blood vessel and a pit pattern (hereinafter, referred to as a tissue and the like structure) contained in a mucous membrane 72 (refer to FIG. 6 and the like), which is a subject in the short wavelength medical images 61 and 62, in a case where the short wavelength medical images 61 and 62 are subjected to Fourier transformation. That is, the red blood cell detection section 41 sets a finer pattern than the tissue and the like structure as a candidate for the red blood cell 71. Since the size of the red blood cell 71 is almost constant, the red blood cell detection section 41 sets the size of a pattern to be a candidate for the red blood cell 71 using the imaging magnification (enlargement ratio) of the subject in the short wavelength medical images 61 and 62.

The term "granular" means that the shape of a pattern is a fine point (including a surface having a small area). That is, the red blood cell detection section 41 removes a linear pattern, such as a blood vessel, and a pattern having a relatively large area compared with the area of the mucous membrane 72 from the red blood cell candidates. Then, the red blood cell detection section 41 sets a spot pattern as a candidate for the red blood cell 71.

The term "high density" refers to having a contrast that can be distinguished from the mucous membrane 72 occupying most of the short wavelength medical images 61 and 62. That is, the red blood cell detection section 41 sets a pattern having a predetermined contrast or more with respect to the mucous membrane 72 as a candidate for the red blood cell 71. Accordingly, the red blood cell detection section 41 can detect the red blood cell 71 even in a case where the short wavelength medical images 61 and 62 are reversed.

More specifically, the red blood cell detection section 41 detects the red blood cell 71 from the short wavelength medical images 61 and 62 using a bottom hat filter using a circular structure, a Quoit filter, or the like. Since the red blood cell has a diameter of about 7 to 8 μm and a thickness of about 2 μm, even in a case where some red blood cells gather, the size is very small. Therefore, except for the case of a special imaging situation in which the red blood cell 71 can be viewed macroscopically by enlarging the subject extremely, it is difficult to detect red blood cells using a medical image (endoscope image). In addition, even in a case where the red blood cell 71 can be detected using a medical image (endoscope image), it is difficult to distinguish red blood cells from noise. On the other hand, the reason why the red blood cell detection section 41 can detect red blood cells while distinguishing the red blood cells from noise by using the short wavelength medical images 61 and 62 is that the short wavelength medical images 61 and 62 are medical images (endoscope images) obtained by imaging the subject with light in a shorter wavelength band than the green wavelength band. In particular, in the present embodiment, the short wavelength medical images 61 and 62 are obtained by imaging the subject with narrowband light that is light in a shorter wavelength band than the green wavelength band and has a very narrow wavelength band. Therefore, even in a case where the situation is not a special imaging situation, it is possible to detect the red blood cell 71 by enlarging and imaging the subject to some extent. In addition, as compared with a case where white light or the like is emitted to the subject to image the subject through a filter that transmits light in the green wavelength band, it is possible to accurately detect the red blood cell 71 in a state with little noise in particular.

The red blood cell quantity calculation section 42 calculates the quantity of red blood cells 71 detected in the short wavelength medical images 61 and 62 using the detection result of the red blood cell detection section 41. The quantity of red blood cells 71 is the number of red blood cells 71 or an amount (area or the like) correlated with the number.

The red blood cell movement amount calculation section 43 calculates the movement amount of the red blood cell 71 detected in the short wavelength medical images 61 and 62 using a series of short wavelength medical images 61 and 62 obtained by detecting the red blood cell 71 by the red blood cell detection section 41. The movement amount of the red blood cell 71 is the movement distance of the red blood cell 71 or an amount (for example, a sum or an average of movement distances) correlated with the movement distance of the red blood cell 71. In the present embodiment, the red blood cell movement amount calculation section 43 calculates a difference between at least two short wavelength medical images, among a series of short wavelength medical images acquired by the medical image acquisition unit 11, for each pixel. Then, the red blood cell movement amount calculation section 43 sums the pixel value difference in each pixel in the entire image or a partial region defined in the image (including calculating the average and other statistics), and sets the absolute value as the movement amount of the red blood cell 71. In a case where two short wavelength medical images are sequentially captured within a short period of time to the extent that the movement amount of the red blood cell 71 can be calculated, the global movement of the mucous membrane 72 is small. Therefore, the sum or the like of differences is correlated with the movement distance of the fast red blood cell 71. That is, the sum or the like of differences between two short wavelength medical images increases as the movement distance of the red blood cell 71 substantially increases.

The index calculation section 44 calculates an index indicating the degree of progress of a lesion using the quantity of red blood cells 71 calculated by the red blood cell quantity calculation section 42 and the movement amount of the red blood cell 71 calculated by the red blood cell movement amount calculation section 43. The lesion is, for example, an inflammatory disease. More specifically, the lesion is an inflammatory bowel disease, such as ulcerative colitis or Crohn's disease occurring in the lower digestive tract. Accordingly the index calculation section 44 calculates an index correlated with the degree of progress of the inflammatory bowel disease.

In particular, in the present embodiment, the index calculation section 44 calculates an index indicating the degree of progress of ulcerative colitis. For the ulcerative colitis, Mayo classification of endoscopic finding classification is known. The Mayo classification has four grades of Mayo0, Mayo1, Mayo2, and Mayo3. Mayo0 is a grade indicating normal or inactive (including a remission period). Mayo1 is a grade indicating mild, and is generally a state in which redness, blood vessel image observer, or slight easy bleeding is recognized. Mayo2 is a grade indicating moderate, and is generally a state in which significant redness, loss of a blood vessel image, easy bleeding, adhesion of purulent secretion, mucosal roughness, erosion, partial ulcer, and the like are recognized. Mayo3 is a grade indicating severe (active phase), and is generally a state in which obvious spontaneous bleeding, edema, ulcer (including a wide range of ulcer), and the like are recognized.

In a case where the degree of progress of ulcerative colitis is approximately Mayo0, the red blood cells 71 densely move in the blood vessel in general in the short wavelength medical images 61 and 62. Therefore, this is excluded from the detection of the red blood cell 71 in the red blood cell detection section 41. In a case where the degree of progress of ulcerative colitis is approximately Mayo1 to Mayo2, the red blood cell 71 leaks into the mucous membrane 72 even in a case where bleeding to the outside of the mucous membrane 72 does not occur. For this reason, in the short wavelength medical images 61 and 62, it is possible to detect the red blood cell 71 moving without following the blood vessel. In a case where the degree of progress of ulcerative colitis is Mayo3, the disease state is clear even without detection of the red blood cell 71 or the like. Therefore, the medical image processing apparatus 10 of the present embodiment determines each grade in the range of Mayo0, Mayo1, and Mayo2, and calculates an index indicating to which grade the state of progress is close.

As an example of the index indicating the degree of progress of a lesion, the index calculation section 44 can calculate a value (hereinafter, referred to as a score) by weighting addition of the quantity of red blood cells 71 and the movement amount of the red blood cell 71. In a case where a lesion is ulcerative colitis, assuming that the quantity of red blood cells 71 is "P1", the movement amount of the red blood cell 71 is "Q1", a weighting coefficient for the quantity P of red blood cells 71 is "$\alpha$", and a weighting coefficient for the movement amount Q of the red blood cell 71 is "$\beta$", a score X1 correlated with the degree of progress of ulcerative colitis is calculated by $X1=\alpha \times P1+\beta \times Q1$. Since the value of the score X1 is correlated with the grade of Mayo classification (for example, as the value becomes larger, the score X1 becomes closer to Mayo2), the correlation with the grade of Mayo classification can be made stronger by adjusting the values of the weighting coefficients $\alpha$ and $\beta$.

Figure 4:
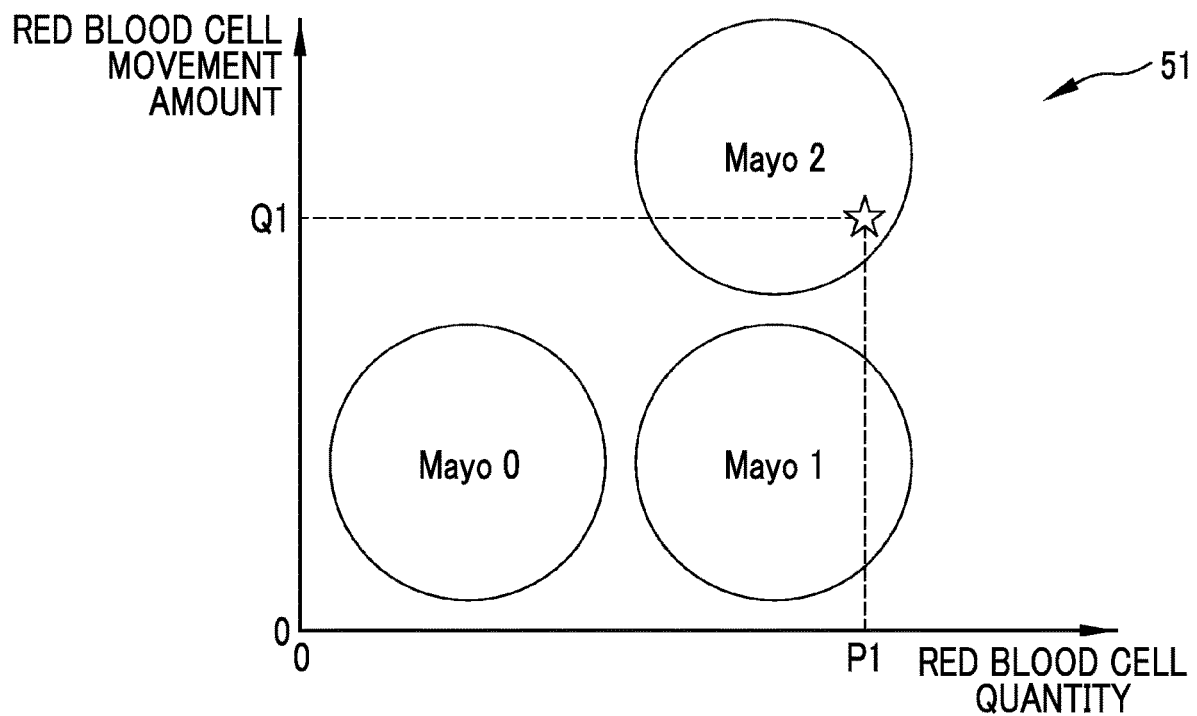
FIG. 4 is a diagram showing the relationship between the quantity and the movement amount of red blood cells and the degree of progress of ulcerative colitis.

The index calculation section 44 can determine the degree of progress of a lesion from the quantity of red blood cells 71 and the movement amount of the red blood cell 71 with reference to a map (including a case of a numerical value table or the like) in which the quantity of red blood cells 71 and the movement amount of the red blood cell 71 are associated with the degree of progress of the lesion. For example, as shown in FIG. 4, it is possible to determine the grade of Mayo classification as the degree of progress of ulcerative colitis by referring to a map 51 in which the quantity of red blood cells 71 and the movement amount of the red blood cell 71 are associated with the degree of progress of the ulcerative colitis. In this case, the grade of Mayo classification is an index calculated by the index calculation section 44. For example, in a case where the quantity of red blood cells 71 is "P1" and the movement amount of the red blood cell 71 is "Q1", the index calculated by the index calculation section 44 is "Mayo2".

The calculation form of the index can be freely switched. In addition, the weighting coefficients $\alpha$ and $\beta$ used for the calculation of the score X1 can also be freely set or changed.

The display unit 13 is a display for displaying the medical image acquired by the medical image acquisition unit 11 and the analysis result of the medical image analysis processing unit 12. A monitor or a display included in a device or the like to which the medical image processing apparatus 10 is connected can be shared and used as the display unit 13 of the medical image processing apparatus 10. The display control unit 15 controls the display form of the medical image and the analysis result on the display unit 13.

The input receiving unit 16 receives inputs from a mouse, a keyboard, and other operation devices attached to the medical image processing apparatus 10. The operation of each unit of the medical image processing apparatus 10 can be controlled using the operation devices.

The overall control unit 17 controls the overall operation of each unit of the medical image processing apparatus 10. In a case where the input receiving unit 16 receives an operation input using an operation device, the overall control unit 17 controls each unit of the medical image processing apparatus 10 according to the operation input.

Figure 7:
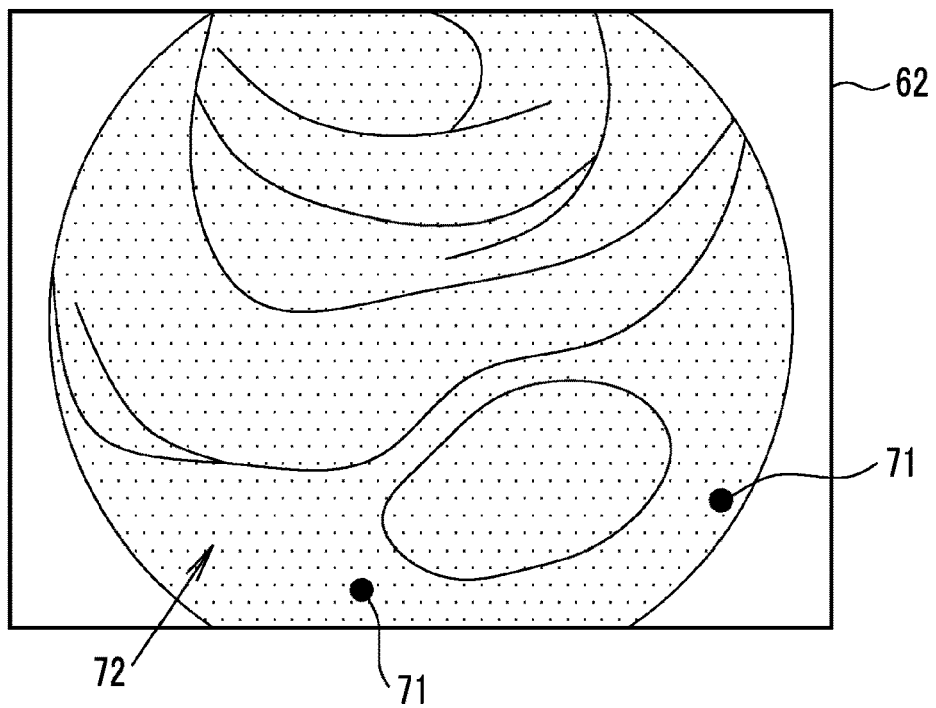
FIG. 7 is a short wavelength medical image captured second between a series of short wavelength medical images.

Hereinafter, a flow of the operation of the medical image processing apparatus 10 will be described. As shown in FIG. 5, the medical image acquisition unit 11 acquires a series of short wavelength medical images 61 and 62 automatically or manually (step S10). As shown in FIG. 6, in the short wavelength medical image 61 captured first between the series of short wavelength medical images 61 and 62, it is possible to detect the red blood cell 71 leaking into the mucous membrane 72. In addition, as shown in FIG. 7, in the short wavelength medical image 62 captured second between the series of short wavelength medical images 61 and 62, the position of the red blood cell 71 moves compared with the first short wavelength medical image 61.

In a case where the medical image acquisition unit 11 acquires a series of short wavelength medical images 61 and 62, the red blood cell detection section 41 detects the red blood cell 71 in each of the series of short wavelength medical images 61 and 62 (step S11). In a case where the red blood cell detection section 41 detects the red blood cell 71 in the series of short wavelength medical images 61 and 62, the red blood cell quantity calculation section 42 calculates the quantity of red blood cells 71 (step S12), and the red blood cell quantity calculation section 42 calculates the movement amount of the red blood cell 71 (step S13). Thereafter, the index calculation section 44 calculates the score X1 correlated with the degree of progress of ulcerative colitis or the grade of Mayo classification as an index using the quantity of red blood cells 71 and the movement amount of the red blood cell 71 (step S14).

Figure 8:
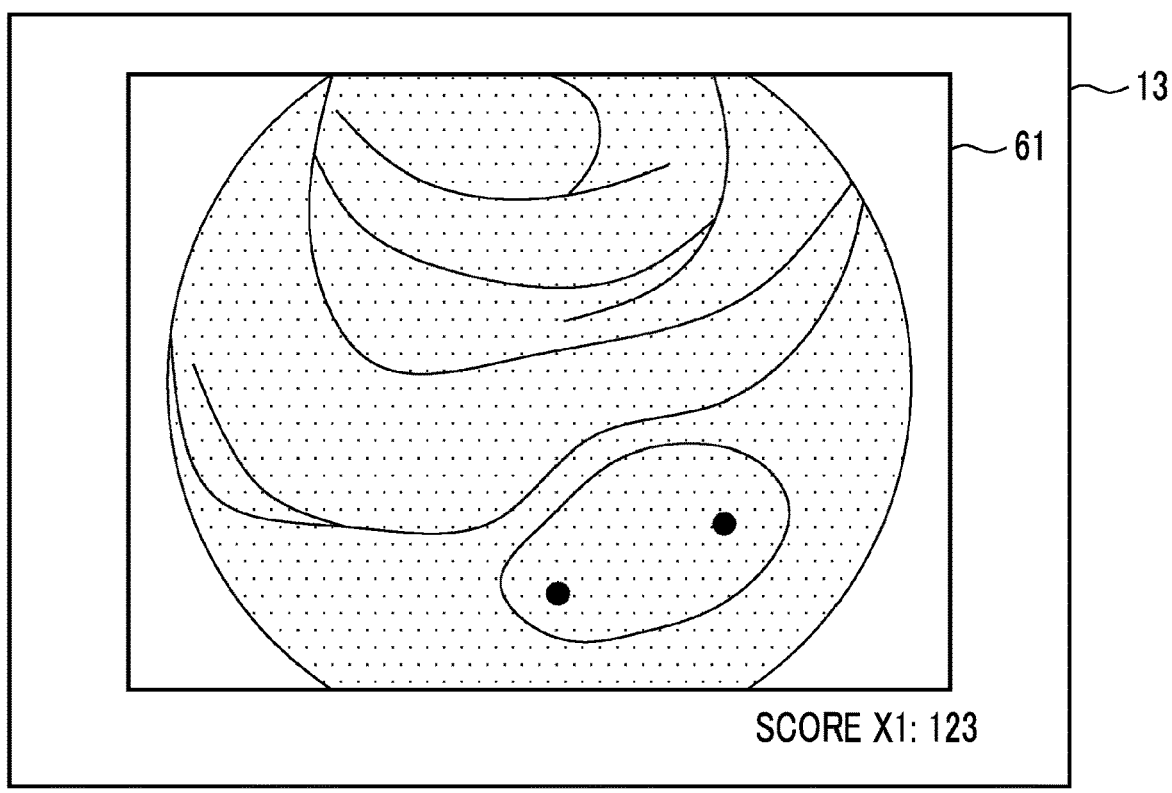
FIG. 8 is a display example on a display unit.
Figure 9:
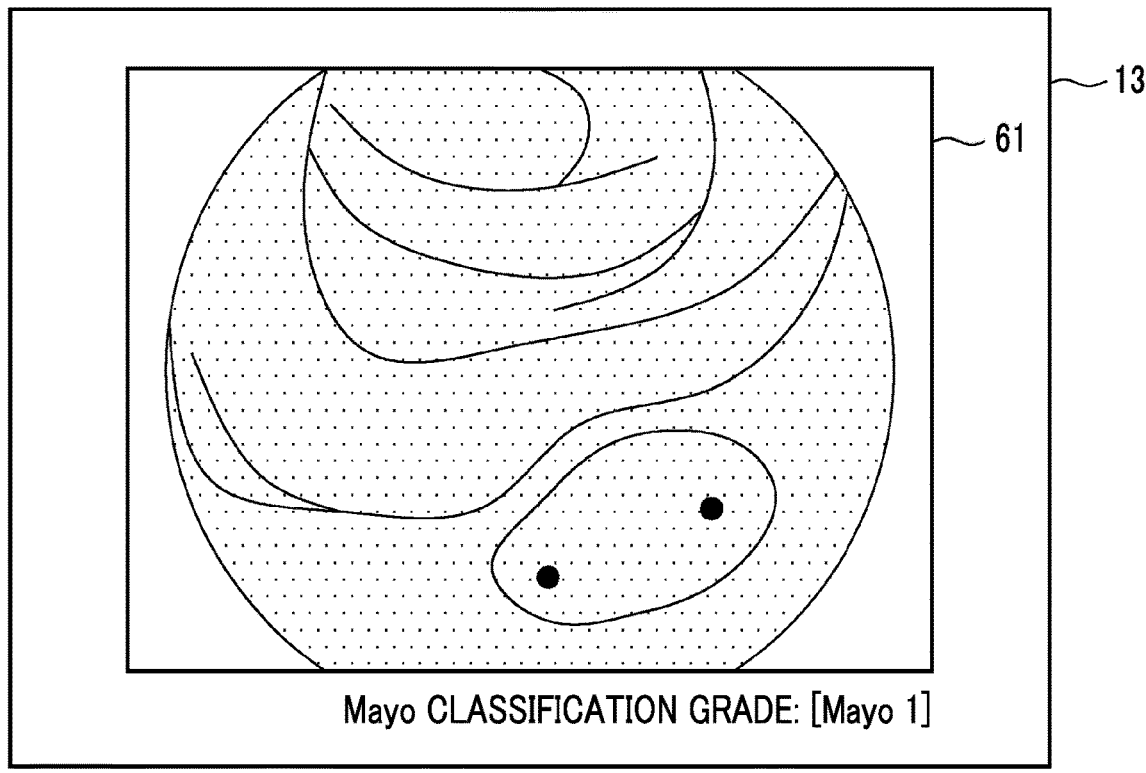
FIG. 9 is a display example on the display unit.

In a case where the index calculation section 44 calculates the score or the grade of Mayo classification as an index, the display control unit 15 displays, on the display unit 13, at least one short wavelength medical image of the series of short wavelength medical images 61 and 62 and the index calculated by the index calculation section 44. In a case where the index calculation section 44 calculates the score X1 correlated with the degree of progress of ulcerative colitis, as shown in FIG. 8, the display control unit 15 displays the short wavelength medical image 61 and the score X1 on the display unit 13, for example. In a case where the index calculation section 44 calculates the grade of Mayo classification, as shown in FIG. 9, the display control unit 15 displays the short wavelength medical image 61 and the grade of Mayo classification on the display unit 13, for example.

As described above, by using the series of short wavelength medical images 61 and 62 obtained by imaging the subject with light in a shorter wavelength band than the green wavelength band, the medical image processing apparatus 10 can detect the red blood cell 71 leaking into the mucous membrane 72, which is normally difficult to accurately detect. As a result, the medical image processing apparatus 10 can obtain an analysis result relevant to the degree of progress of a lesion that has been difficult to determine in the related art, such as the degree of progress of ulcerative colitis, using the detected quantity of red blood cells 71 and the detected movement amount of the red blood cell 71. In particular, in the inflammatory bowel disease, such as ulcerative colitis and Crohn's disease, it has been difficult to accurately determine the grade of the disease as approximately mild to moderate. However, the medical image processing apparatus 10 can provide an index by which the diseases can be more accurately determined than in the related art. In the embodiment described above, by using the index calculated by the medical image processing apparatus 10, it is possible to specifically and objectively determine Mayo1 and Mayo2 or Mayo0 and Mayo1 in ulcerative colitis or to what extent the disease is close to each grade (Mayo1 close to Mayo2, Mayo1 close to Mayo0, and the like).

In the embodiment described above, the red blood cell movement amount calculation section 43 sums up the differences between the two short wavelength medical images 61 and 62 and calculates the absolute value as the movement amount of the red blood cell 71. However, the red blood cell movement amount calculation section 43 can calculate the movement amount of the red blood cell 71 using a method different from the first embodiment described above. For example, by performing pattern matching between the short wavelength medical image 61 captured first and the short wavelength medical image 62 captured second to detect the corresponding red blood cell 71, the movement amount of each red blood cell 71 may be calculated.

In the embodiment described above, the imaging magnification of the series of short wavelength medical images 61 and 62 can be set freely. However, it is preferable that the series of short wavelength medical images 61 and 62 are short wavelength medical images captured by enlarging the subject 60 times or more on the 19-inch display screen. In this case, the red blood cell 71 can be accurately detected using the series of short wavelength medical images 61 and 62. In addition, the imaging magnification is an imaging magnification at the time of one step zooming in an endoscope for a digestive tract having a general zoom function.

Figure 10:
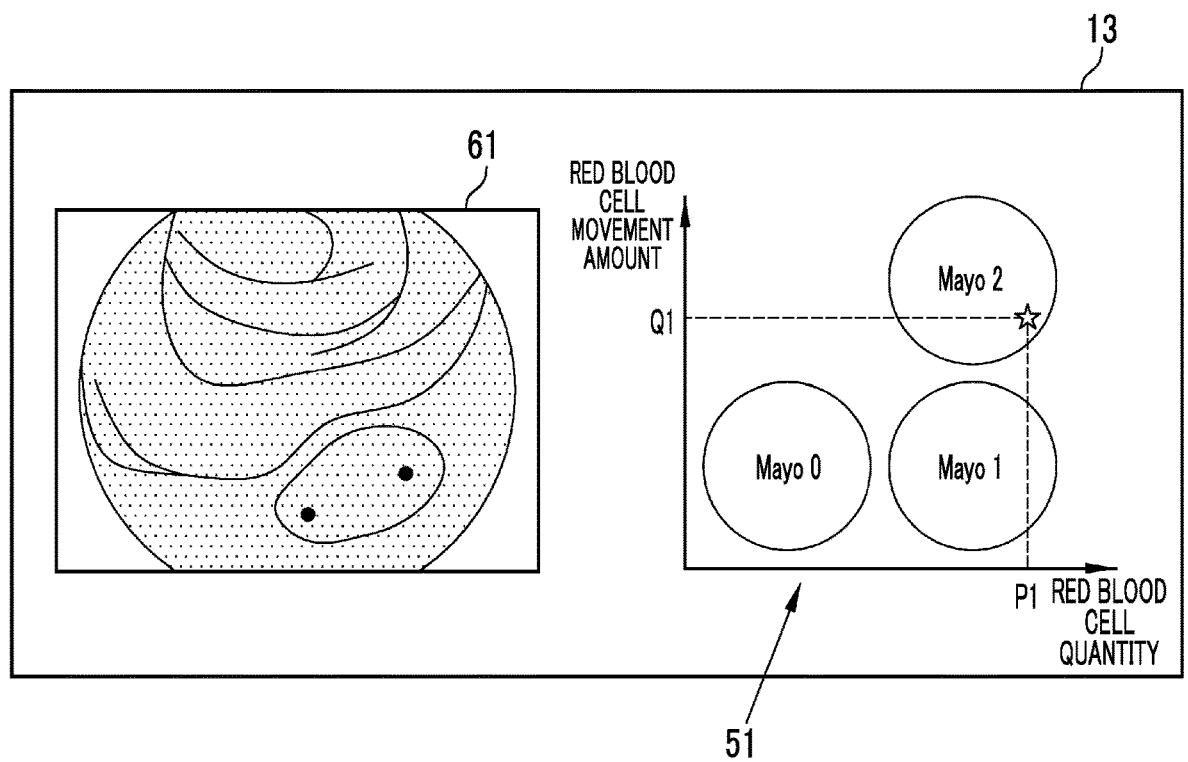
FIG. 10 is a display example on the display unit.

In the embodiment described above, the display control unit 15 displays the short wavelength medical image 61 and the score X1 or the grade of Mayo classification on the display unit 13. However, this display form is merely an example, and these pieces of information can be displayed on the display unit 13 in another display form. For example, in a case where any of the score X1 and the grade of Mayo classification is calculated as an index, as shown in FIG. 10, the display control unit 15 can display the short wavelength medical image 61 and the map 51, in which the quantity of red blood cells 71 and the movement amount of the red blood cell 71 are associated with the grade of the Mayo classification, on the display unit 13 so that the specific quantity "P1" and movement amount "Q1" of the red blood cell 71 and the corresponding position (star mark) in the map 51 are shown on the map 51. At least the display forms of the display unit 13 shown in FIGS. 9 and 10 are display forms in which the degree of progress of a lesion can be directly recognized. In this respect, at least the display forms of the display unit 13 shown in FIGS. 9 and 10 are display forms in which the degree of progress of a lesion and the index are displayed so as to be associated with each other.

In the embodiment described above, since the short wavelength medical image 61 is an image captured using so-called narrowband light and there is information in only about B channel (blue channel), the display control unit 15 displays the image on the display unit 13 in gray scale. However, the display control unit 15 can display the short wavelength medical images 61 and 62 on the display unit 13 in color.

Figure 11:
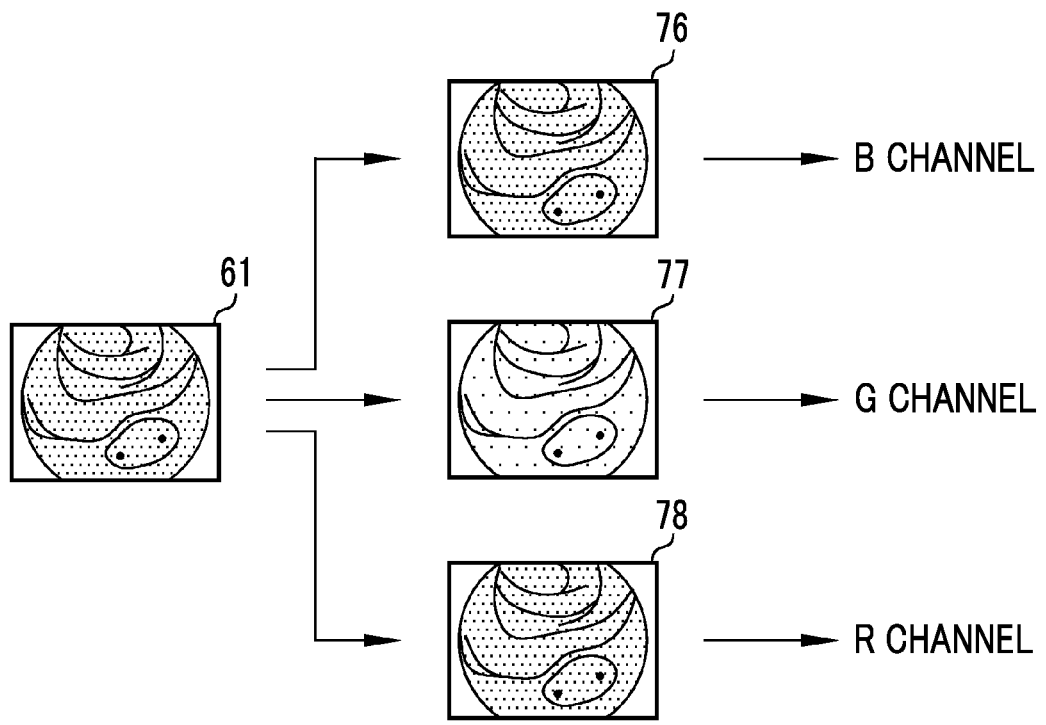
FIG. 11 is an explanatory diagram showing the operation of a display control unit.

In the case of displaying the short wavelength medical images 61 and 62 on the display unit 13 in color, the display control unit 15 functions as a display color adjustment unit that adjusts the display color of the short wavelength medical images 61 and 62 displayed on the display unit 13. For example, in the case of displaying the short wavelength medical image 61 on the display unit 13, as shown in FIG. 11, the display control unit 15 assigns the short wavelength medical image 61 displayed on the display unit 13 to a B channel (blue channel), a G channel (green channel), and an R channel (red channel) for display. In this case, the display control unit 15 performs correction for each color channel on the grayscale short wavelength medical image 61, which is an input source, for at least one color channel, and then outputs the obtained image to each color channel. That is, the display control unit 15 generates a B channel image 76 after B channel correction, a G channel image 77 after G channel correction, and an R channel image 78 from the input short wavelength medical image 61, and displays the pseudo-colored short wavelength medical image 61 on the display unit 13 by using these.

Figure 12:
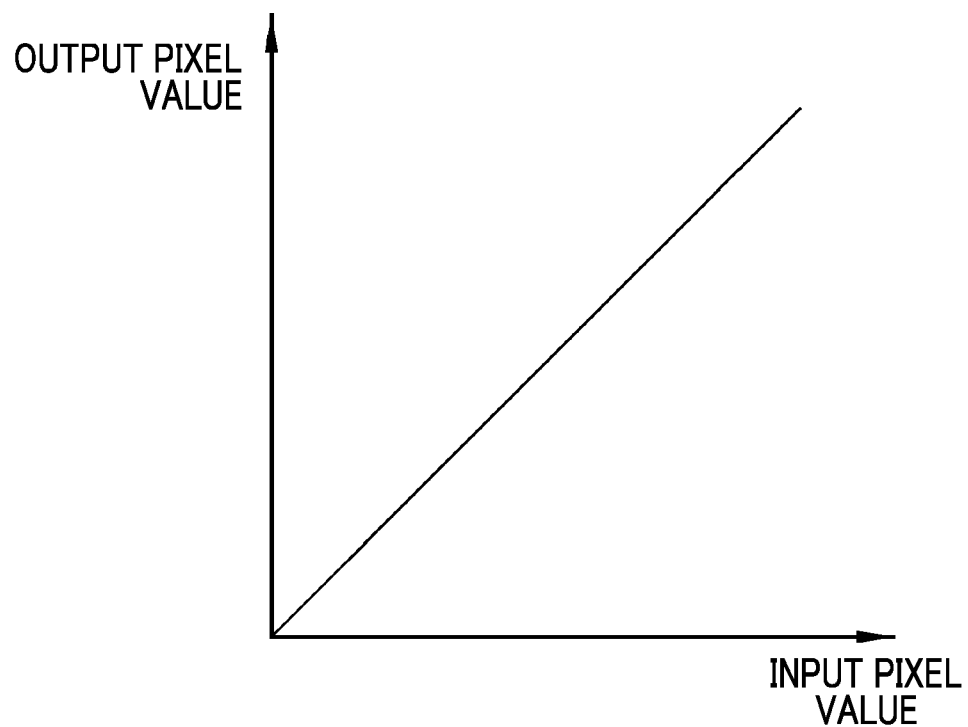
FIG. 12 is a graph showing the relationship between input and output.
Figure 13:
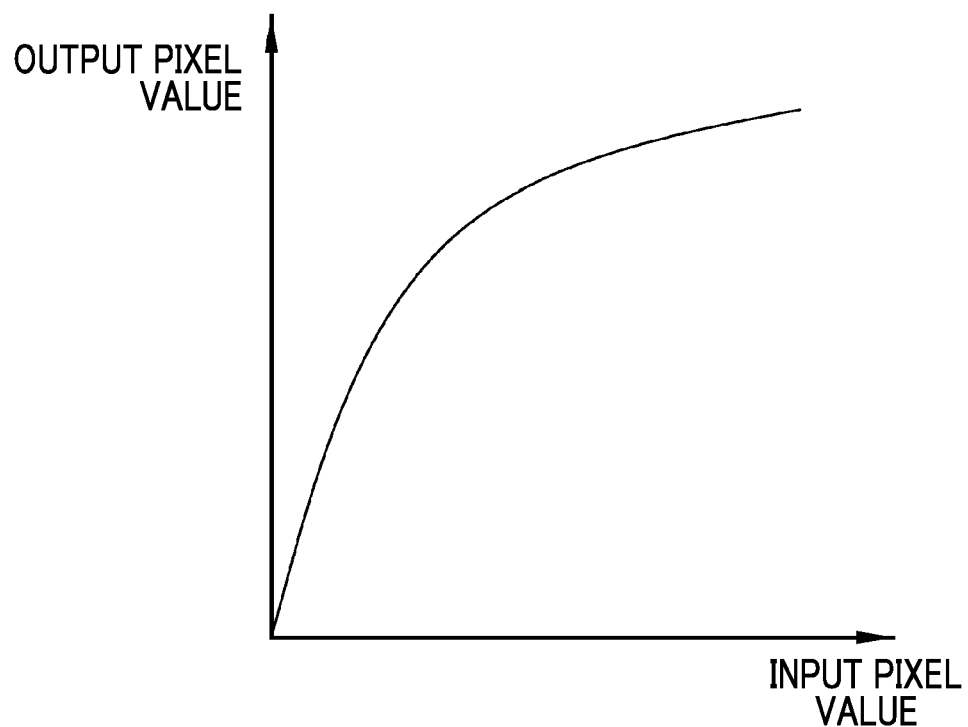
FIG. 13 is a graph showing the relationship between input and output.
Figure 14:
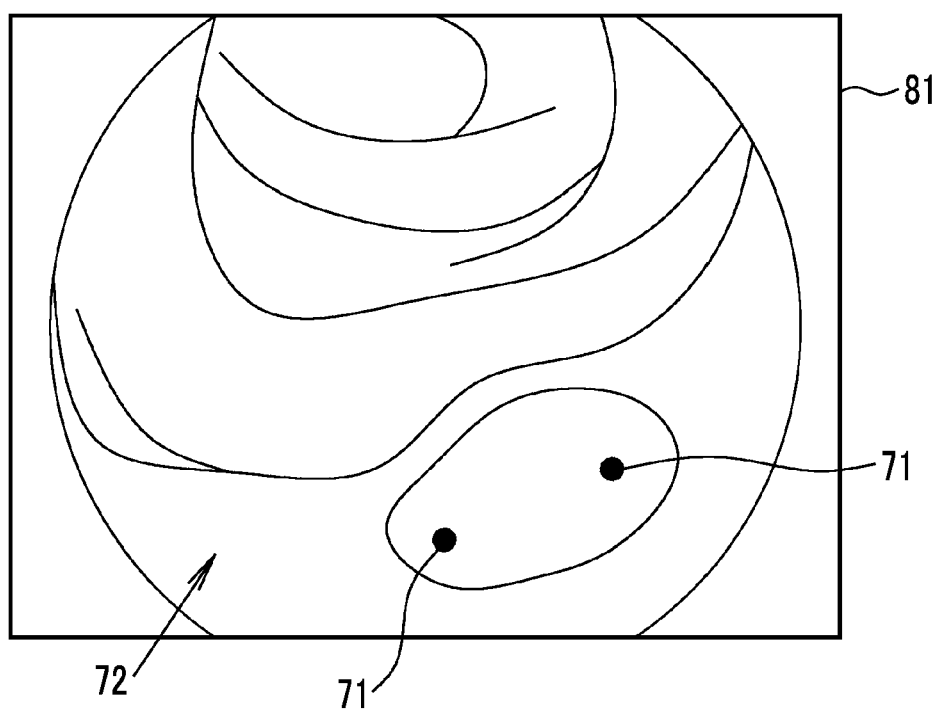
FIG. 14 is an endoscope image after color tone adjustment.

More specifically, for example, for the B channel and the R channel, the display control unit 15 linearly associates the input pixel value and the output pixel value with each other as shown in FIG. 12. For this reason, the short wavelength medical image 61 as an input source is output as it is without substantially performing correction for the B channel and the R channel. Then, for the G channel, for example, as shown in FIG. 13, correction is made so as to nonlinearly associate the input pixel value and the output pixel value with each other. In these results, the color of the mucous membrane 72 becomes a green color. On the other hand, since the red blood cell 71 absorbs light in a short wavelength band satisfactorily, the red blood cell 71 is almost black in the grayscale short wavelength medical image 61 that is an input source. Therefore, even after the above correction, the color of the red blood cell 71 is almost black. As a result, as shown in FIG. 14, in a display image 81 in which the color of the mucous membrane 72 is a green color, the contrast of the red blood cell 71 with respect to the mucous membrane 72 is higher than in the original short wavelength medical image 61. Therefore, the red blood cell 71 can be easily recognized. This is also apparent from the fact that, in the Lab color space in consideration of the balance of human vision, the color difference between the green color of the mucous membrane 72 and the black color of the red blood cell 71 in the display image 81 is higher than the color difference between the white color of the mucous membrane 72 and the black color of the red blood cell 71 in the grayscale short wavelength medical image 61. In addition, since a doctor or the like is familiar with a medical image emphasizing a blood vessel and the like (so-called narrowband observation image and the like), the color of the mucous membrane 72 in such a medical image is a green-based color in many cases. Accordingly, there is also an advantage that, by making the mucous membrane 72 in green color in the display image 81 as described above, the image can be displayed with less discomfort than medical images of other general display forms while coloring in a pseudo manner.

Figure 15:
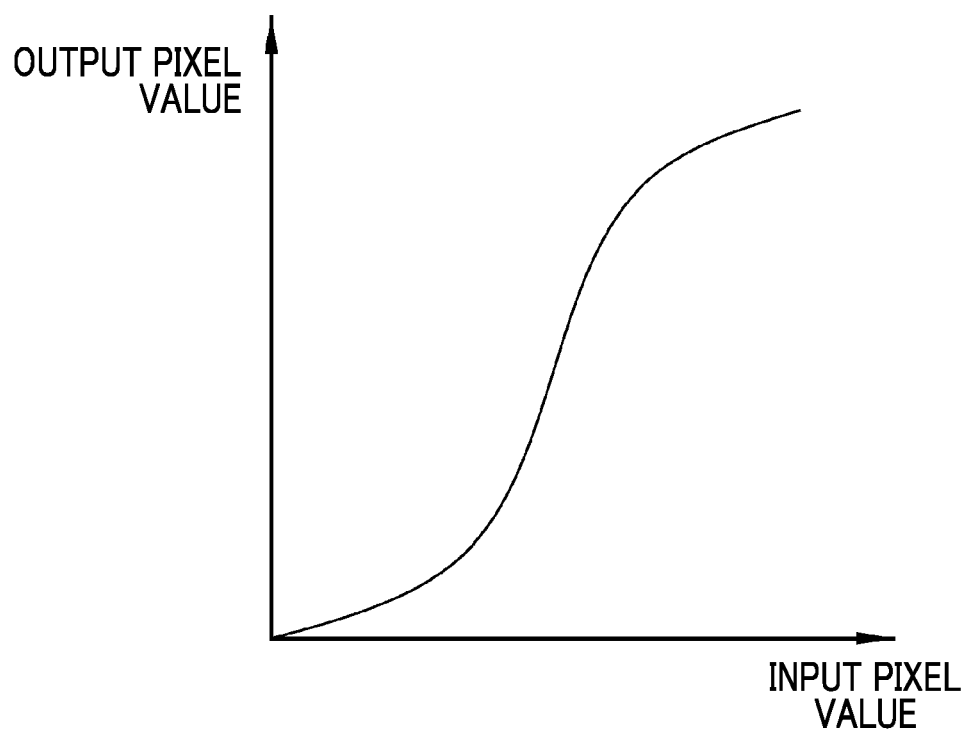
FIG. 15 is a graph showing the relationship between input and output.
Figure 16:
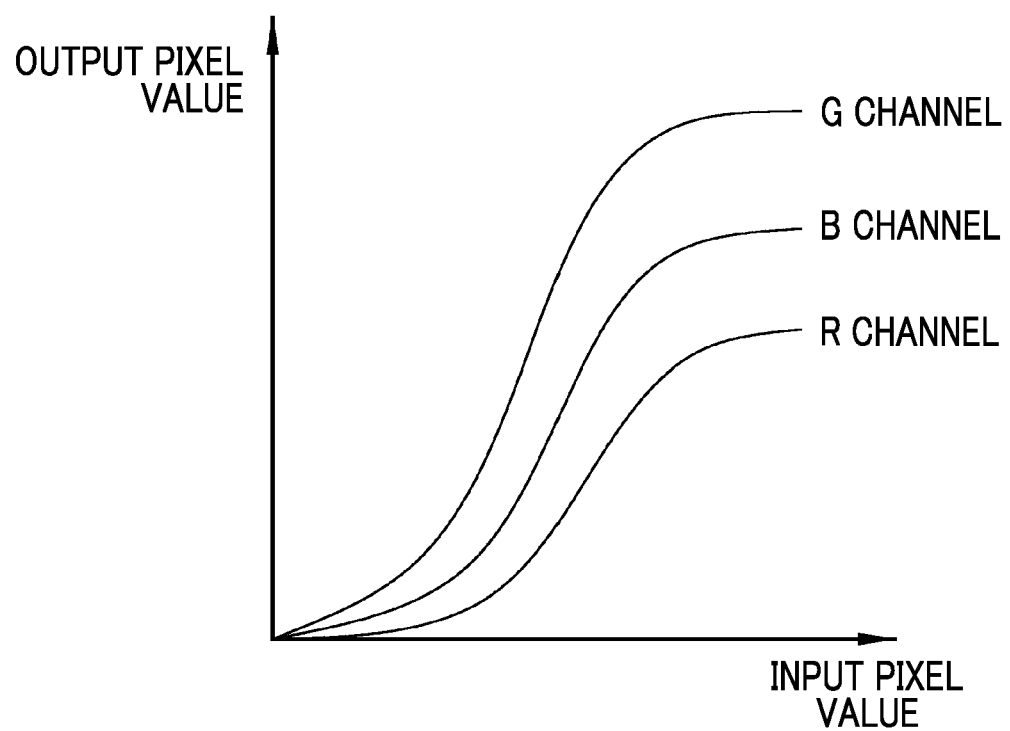
FIG. 16 is a graph showing the relationship between input and output.

The correction for nonlinear association is not limited to the example described above. For example, as shown in FIG. 15, an S-shaped curve may be used in order to improve the visibility of an intermediate density signal. Also in this case, as shown in FIG. 16, separate conversion tables may be assigned to the R channel, the G channel and the B channel. In addition, adjustment may be made by multiplying the grayscale short wavelength medical image 61, which is an input source, by a gain as a correction for each color channel. In this case, the gain assigned to the G channel is set to be high, and the gain assigned to the R channel and the B channel is set to be low.

In the above embodiment and modification examples, short wavelength medical image 61 or the display image 81 in which the short wavelength medical image 61 is pseudo-colored is displayed on the display unit 13. However, the display control unit 15 can display other medical images on the display unit 13. For example, the medical image acquisition unit 11 acquires a medical image to be used for display on the display unit 13 in addition to the series of short wavelength medical images 61 and 62. The medical image to be used for display on the display unit 13 is, for example, a medical image captured by emitting white light to the subject, and is an endoscope image (hereinafter, referred to as a white light image) captured almost simultaneously with any of the series of short wavelength medical images 61 and 62 (at time intervals at which there is no large change in the mucous membrane 72 and the like). In this case, the display control unit 15 can display the white light image on the display unit 13 instead of the series of short wavelength medical images 61 and 62 used for detection of the red blood cell 71 or the like. In addition, the display control unit 15 can highlight the position of the red blood cell 71 on the white light image by displaying the detection result of the red blood cell detection section 41 on the display unit 13 so as to overlap the white light image.

Figure 17:
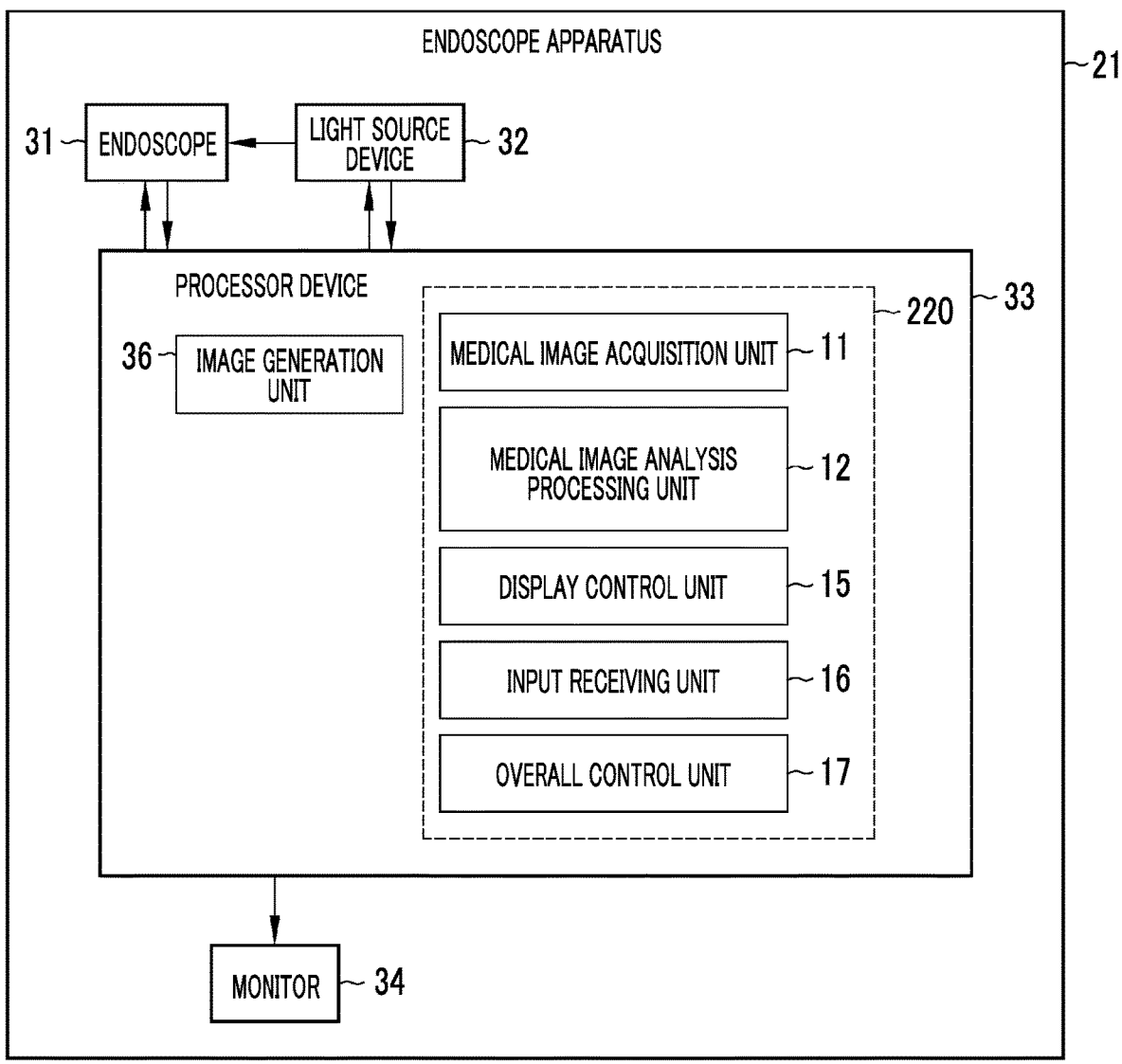
FIG. 17 is a block diagram of an endoscope apparatus including a medical image processing apparatus.

In the embodiment described above, the medical image processing apparatus 10 and the endoscope apparatus 21 are separate apparatuses. However, the endoscope apparatus 21 can include the medical image processing apparatus 10. In this case, as shown in FIG. 17, each unit 220 forming the medical image processing apparatus 10 is provided in the processor device 33. However, since the monitor 34 of the endoscope apparatus 21 can be shared as the display unit 13, it is sufficient to provide each unit other than the display unit 13 in the processor device 33. In addition, a new endoscope apparatus can be configured by all of the medical image processing apparatuses 10 of the above embodiment and other modification examples and the endoscope apparatus 21 shown in FIG. 2.

Basically, the endoscope apparatus 21 is an apparatus for observing the subject in real time. As described above, in a case where the endoscope apparatus 21 includes the medical image processing apparatus 10, detection of the red blood cell 71 and the calculation of an index can be performed at any timing by automatic or manual setting.

Figure 18:
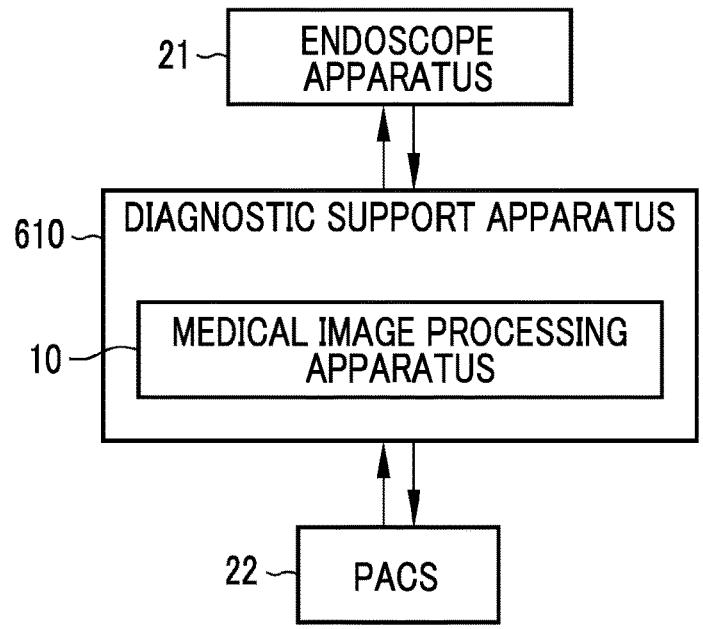
FIG. 18 is a diagnostic support apparatus including a medical image processing apparatus.
Figure 19:
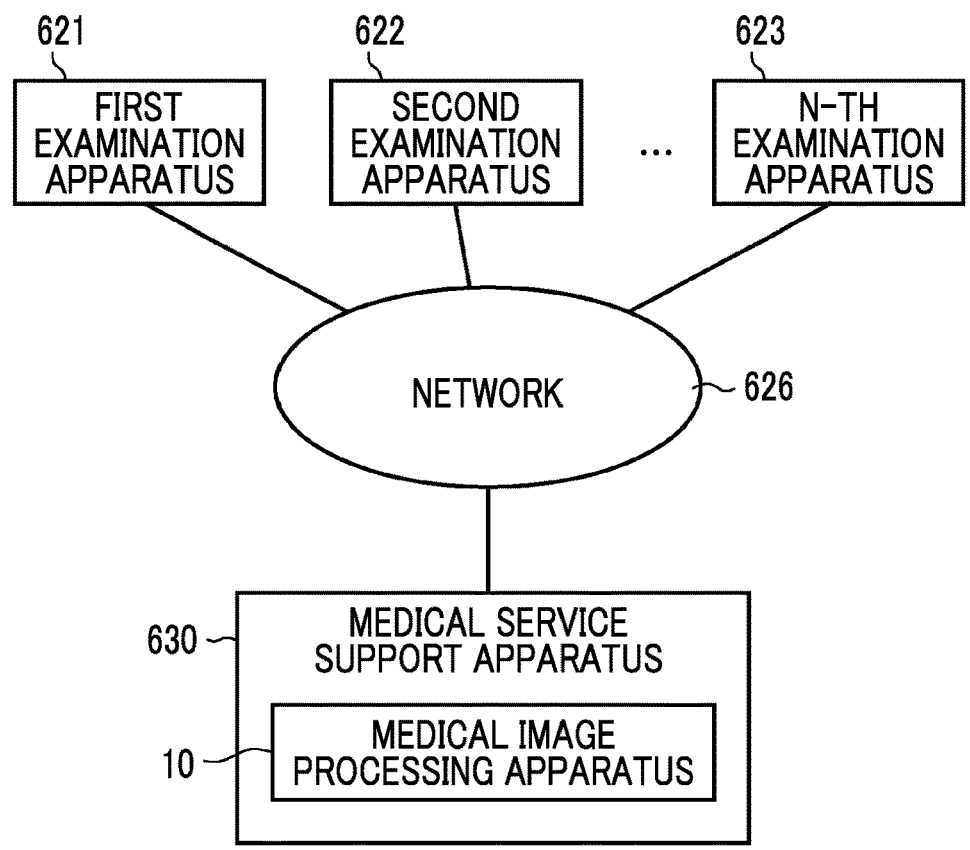
FIG. 19 is a medical service support apparatus including a medical image processing apparatus.

As shown in FIG. 18, a diagnostic support apparatus 610 used in combination with the endoscope apparatus 21 and other modalities can include the medical image processing apparatuses 10 of the above embodiment and other modification examples. In addition, as shown in FIG. 19, for example, a medical service support apparatus 630 connected to various examination apparatuses including the endoscope apparatus 21, such as a first examination apparatus 621, a second examination apparatus 622, . . . , and an N-th examination apparatus 623, through a certain network 626 can include the medical image processing apparatuses 10 of the above embodiment and other modification examples.

The medical image processing apparatus 10, various apparatuses including the medical image processing apparatus 10, and various apparatuses or systems having the function of the medical image processing apparatus 10 can be used by making the following various changes or the like.

In a case where a region of interest detection section that detects a region of interest, which is a region to be observed, based on the feature amount of the pixels of the short wavelength medical images 61 and 62 is provided, the red blood cell detection section 41 can detect the red blood cell 71 in a region of interest.

In the endoscope apparatus 21, a capsule endoscope can be used as the endoscope 31. In this case, the light source device 32 and a part of the processor device 33 can be mounted in the capsule endoscope.

The index calculation section 44 can calculate indices other than the indices shown in the above embodiment and modification examples. For example, the index calculation section 44 can calculate information regarding blood vessels (hereinafter, referred to as blood vessel information), such as the thickness, the number, or the density of blood vessels, using the series of short wavelength medical images 61 and 62 or other medical images acquired by the medical image acquisition unit 11. As described above, in a case where the index calculation section 44 calculates indices other than the indices shown in the above embodiment and modification examples, such as blood vessel information, the display control unit 15 can display the indices other than the indices shown in the above embodiment and modification examples on the display unit 13 together with the indices shown in the above embodiment and modification examples. In addition, display or non-display of indices other than the indices shown in the above embodiment and modification examples can be freely switched by user's setting or operation.

The medical image processing apparatus 10 can store the analysis result (the position of the red blood cell 71, the quantity of red blood cells 71, the movement amount of the red blood cell 71, and the index calculated using these) of the medical image analysis processing unit 12 in the PACS 22 or any other storage. In this case, the series of short wavelength medical images 61 and 62 used for the analysis and the analysis result can be stored so as to be associated with each other.

In the above embodiment and modification examples, the hardware structures of processing units for executing various kinds of processing, such as the medical image acquisition unit 11, the medical image analysis processing unit 12, each unit forming the medical image analysis processing unit 12, the display control unit 15, the input receiving unit 16, the overall control unit 17, and the image generation unit 36, are various processors shown below. The various processors include: a central processing unit (CPU) that is a general-purpose processor that functions as various processing units by executing software; a programmable logic device (PLD) that is a processor whose circuit configuration can be changed after manufacture, such as field programmable gate array (FPGA), a dedicated electrical circuit that is a processor having a dedicated circuit configuration for executing various types of processing; and the like.

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, so represented by a computer, such as a client or a server, there is a form in that one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

The medical image processing apparatus 10 of the above embodiment and modification examples can be suitably used not only for the purpose of determining the degree of progress of an inflammatory disease but also for the purpose of checking the presence or absence of bleeding from a sutured part after surgery. In addition, the medical image processing apparatus 10 is also suitable for determining the degree of progress of an inflammatory disease in the upper digestive tract, such as the esophagus, as well as an inflammatory bowel disease in the lower digestive tract.

The display forms of medical images shown in FIGS. 11 to 14 can be used separately from the detection function of the red blood cell 71 of the medical image processing apparatus 10 and the like. The display forms of medical images shown in FIGS. 11 to 14 are useful in the case of displaying a grayscale endoscope image on the display unit 13 or the like. For example, in the general endoscope apparatus 21, in the case of displaying a grayscale endoscope image on the monitor 34, the grayscale endoscope image can be displayed in a pseudo-color manner in the display forms of medical images shown in FIGS. 11 to 14. In this case, even in a case where the red blood cell 71 is not reflected, the visibility of a portion, which is approximately black in the original grayscale medical image, can be improved. In the embodiment and the like described above, in the case of displaying the grayscale short wavelength medical image 61 as an input source on the display unit 13, the display control unit 15 adjusts the display color. However, the display image 81 can be generated in advance. That is, a correction unit that performs correction corresponding to each color channel in the case of assigning a grayscale image as an input source to a plurality of color channels (RGB or CMYK) and a pseudo-color image generation unit that generates a new image in which an original grayscale image is pseudo-colored using a corrected image are provided. Then, the display control unit 15 may display the pseudo-color image (display image 81) generated by the pseudo-color image generation unit on the display unit 13. Needless to say, also in the medical image processing apparatus 10, the correction unit and the pseudo-color image generation unit can be provided.

EXPLANATION OF REFERENCES

10: medical image processing apparatus
11: medical image acquisition unit
12: medical image analysis processing unit
13: display unit
15: display control unit
16: input receiving unit
17: overall control unit
21: endoscope apparatus
22: PACS
31: endoscope
32: light source device
33: processor device 34: monitor
36: image generation unit
41: red blood cell detection section
42: red blood cell quantity calculation section
43: red blood cell movement amount calculation section
44: index calculation section
51: map
61, 62: short wavelength medical image
71: red blood cell
72: mucous membrane
76: B channel image
77: G channel image
78: R channel image
81: display image
220: each unit forming medical image processing apparatus
610: diagnostic support apparatus
621: first examination apparatus
622: second examination apparatus
623: N-th examination apparatus
626: network
630: medical service support apparatus
P1: quantity of red blood cells
Q1: movement amount of red blood cell
X1: score

What is claimed is:

1. A medical image processing apparatus comprising:
a processor configured to:
acquire a short wavelength medical image, which is a medical image including a subject image and which is obtained by imaging a subject with a light in a shorter wavelength band than a green wavelength band;
detect a red blood cell using the short wavelength medical image;
calculate a quantity of red blood cells detected in the short wavelength medical image;
calculate a movement amount of red blood cells detected in the short wavelength medical image; and
calculate an index indicating a degree of progress of a lesion using the quantity and the movement amount of red blood cells,
wherein the processor calculates the index correlated with a degree of progress of an inflammatory bowel disease.

2. The medical image processing apparatus according to claim 1,
wherein processor detects a high-frequency, granular, and high-density region as a red blood cell using the short wavelength medical image.

3. The medical image processing apparatus according to claim 1,
wherein the processor calculates the movement amount of red blood cells using a series of the short wavelength medical images in which red blood cells are detected by the processor.

4. The medical image processing apparatus according to claim 3,
wherein the processor calculates the movement amount of red blood cells using two of the short wavelength medical images captured consecutively or two of the short wavelength medical images captured at specific intervals.

5. The medical image processing apparatus according to claim 1,
wherein the processor calculates the index by weighting addition of the quantity and the movement amount.

6. The medical image processing apparatus according to claim 1, further comprising:
a display that displays the short wavelength medical image,
wherein the processor is further configured to adjust a display color of the short wavelength medical image displayed on the display.

7. The medical image processing apparatus according to claim 6,
wherein the processor sets a color of a mucous membrane as a green color.

8. The medical image processing apparatus according to claim 1,
wherein the processor is further configured to detect a region of interest, which is a region to be observed, based on a feature amount of pixels of the short wavelength medical image,
wherein the processor detects a red blood cell in the region of interest.

9. The medical image processing apparatus according to claim 1,
wherein the short wavelength medical image is an image obtained by emitting light in a specific wavelength band.

10. The medical image processing apparatus according to claim 9,
wherein the specific wavelength band is a blue band or a violet band of a visible range.

11. The medical image processing apparatus according to claim 10,
wherein the light in the specific wavelength band has a peak at 390 nm or more and 450 nm or less.

12. An endoscope apparatus, comprising:
the medical image processing apparatus according to claim 1; and
an endoscope that acquires an image by emitting light in the short wavelength band.

13. A diagnostic support apparatus comprising the medical image processing apparatus according to claim 1.

14. A medical service support apparatus comprising the medical image processing apparatus according to claim 1.

15. The medical image processing apparatus according to claim 1, further comprising:
a display that displays the degree of progress of the lesion and the index so as to be associated with each other.

* * * * *